United States Patent [19]

Simonson, III et al.

[11] Patent Number: 4,929,314

[45] Date of Patent: May 29, 1990

[54] COULOMETRIC TITRATOR APPARATUS AND METHOD

[75] Inventors: Frederick Simonson, III, Port Allen; Timothy M. Gunn, Baton Rouge, both of La.

[73] Assignee: The Dow Chemical Company, Midland, Mich.

[21] Appl. No.: 376,823

[22] Filed: Jul. 7, 1989

[51] Int. Cl.[5] ............................................. G01N 27/42
[52] U.S. Cl. ................................ 204/153.23; 204/405; 204/153.2; 204/153.22; 436/42
[58] Field of Search ............ 204/405, 1 M, 1 K, 1 W; 436/39, 42

[56] References Cited

U.S. PATENT DOCUMENTS

| | | | |
|---|---|---|---|
| 2,583,454 | 1/1952 | Wiese | 436/42 |
| 3,026,182 | 3/1962 | Jankowski et al. | 436/51 |
| 3,363,990 | 1/1968 | Blom et al. | 423/352 |
| 3,461,042 | 8/1969 | Martin et al. | 204/1 T |
| 3,578,408 | 5/1971 | Sirois et al. | 166/307 |
| 3,616,273 | 10/1973 | Olta | 204/1 T |
| 3,726,778 | 4/1973 | Levy et al. | 204/1 T X |
| 3,730,685 | 5/1973 | Prohaska | 436/51 |
| 4,012,197 | 3/1977 | Howarth | 436/150 |
| 4,749,552 | 6/1988 | Sakisako et al. | 422/75 |
| 4,802,957 | 2/1989 | Kuwata et al. | 204/1 T |

Primary Examiner—G. L. Kaplan
Attorney, Agent, or Firm—William J. Coughlin

[57] ABSTRACT

A high pressure coulometric titration apparatus features a pressure vessel for containing a titration vessel, which is capable of being subjected to a pressure above the vaporization pressure of the sample to be analyzed. A back pressure regulator is employed to maintain the internal chamber created by the pressure vessel at this predetermined pressure level, so that the sample will remain in a liquid phase throughout the analysis. A fluid control arrangement is also provided for sweeping the chamber with a dry, inert gas, as well as conveying a predetermined amount of the sample to the titration vessel. This fluid control arrangement in combination with the pressure vessel operates to insure that all of the water in the sample will be trapped in the solvent, as well as to prevent the introduction of extraneous water into the system.

15 Claims, 4 Drawing Sheets

COULOMETRIC TITRATOR APPARATUS AND METHOD

BACKGROUND OF THE INVENTION

The present invention relates generally to coulometric titration, and more particularly to an apparatus and method for analyzing the water content in chemicals which have a relatively high vapor pressure level or which boil below atmospheric temperature, such as methyl chloride.

During the production of certain chemicals, it would be beneficial to determine the amount of particular trace constituents, such as the content of water in methyl chloride. However, providing an accurate and reproducible method of analysis is often difficult and quite operator dependent. This is particularly true with respect to the analysis of water in methyl chloride.

As is well known, methyl chloride will generate approximately 75 pounds of pressure under atmospheric or ambient temperature conditions. In other words, if a cylinder containing liquid methyl chloride is opened to the atmosphere in ambient laboratory conditions (e.g., 70°–80° f) it will supercool itself down to −24.5 degrees centigrade. Thus, methyl chloride has a boiling point of −24.5 degrees centigrade.

In general, the water content of methyl chloride is usually analyzed in the industry by Karl Fischer titration. This process typically involves bringing a cylinder containing a supply of methyl chloride into an analytical laboratory, weighing the cylinder, and dispersing a small sample into a titration vessel. As the cylinder is cracked open, the methyl chloride changes from a liquid into a gas as it encounters atmospheric conditions. Specifically, the methyl chloride is bubbled into the solvent contained in the titration vessel, and hopefully all of the water in the methyl chloride will be trapped in this solvent. The sample of methyl chloride or titrand is then subjected to conventional titration analysis.

In this regard, Karl Fischer's method depends on the use of a special reagent, consisting of iodine, sulphur dioxide, and pyridine. In the presence of water, the $SO_2$ is oxidized by the iodine to $SO_3$ from which sulphuric acid is formed with water.

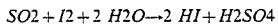

$$SO_2 + I_2 + 2\ H_2O \rightarrow 2\ HI + H_2SO_4$$

The acid components (hydriodic and sulphuric acids) are taken up by the pyridine. When all the water has been consumed in this manner, free iodine remains in the solution, giving rise to the changes in current or voltage. This end point voltage is determined by a two platinum electrode and is referred to as dead-stop or biamperometric method.

With coulometric titration, the process is similar in principal, except that the titration vessel includes an electrode assembly for generating its own pyridine to neutralize the water. There are two basic advantages of coulometric titration when compared to standard Karl Fischer titration. Firstly, with coulometric titration, there is no need to repeatedly calibrate the reagent during the process. Whereas, with Karl Fischer titration, reagent is continuously added, so that there is a possibility that moisture will contaminate the reagent. Additionally, coulometric titration typically requires a much smaller amount of the sample to work with, and therefore, the analytical process is considerably faster when compared with Karl Fischer titration.

Nevertheless, even with coulometric titration, it is difficult to obtain accurate and repeatable results when analyzing the water content in methyl chloride. This is due in large part to the fact that methyl chloride boils at such a low temperature, as it has relatively high vapor pressure. For example, when the methyl chloride cylinder is cracked open, it is possible to transfer too much methyl chloride, and therefore not all of the water will be trapped in the solvent. Additionally, as the methyl chloride enters the gas phase, it will be chilling the tube downstream of the valve being cracked open, and it is possible for water to be added to the system due to this refrigeration effect. Furthermore, methyl chloride is hydroscopic. Accordingly, as a dry chemical, it will draw in moisture to itself, and this has made it almost impossible to achieve good results with commercial titration equipment for methyl chloride samples having a water content below 10 ppm.

Therefore, it is a principal objective of the present invention to provide a titration method and system for analyzing the water content in chemicals such as methyl chloride which will achieve reproducible and accurate results.

It is another objective of the present invention to achieve a method and system of titration analysis which is not technique or operator dependent in terms of obtaining accurate and reproducible readings.

It is a further objective of the present invention to provide a method and system of titration analysis which can achieve relatively quick results and be capable of automation for process control for chemical production.

It is an additional objective of the present invention to provide a method and system of titration which is capable of determining the water content in hydroscopic chemicals down below 10 ppm.

It is yet another objective of the present invention to provide a method and system of titration analysis which is capable of utilizing existing titration vessels and coulometric analyzers.

SUMMARY OF THE INVENTION

To achieve the foregoing objectives, the present invention features a pressure vessel for containing a titration vessel, which is capable of being subjected to a pressure above the vaporization pressure of the sample to be analyzed. A back pressure regulator is employed to maintain the internal chamber created by the pressure vessel at this predetermined pressure level, so that the sample will remain in a liquid phase throughout the analysis. A fluid control arrangement is also provided for sweeping the chamber with a dry, inert gas, as well as conveying a predetermined amount of the sample to the titration vessel. This fluid control arrangement in combination with the pressure vessel operates to insure that all of the water in the sample will be trapped in the solvent, as well as to prevent the introduction of extraneous water into the system. Thus, accurate and reproducible results can be achieved, even for water contents below 10 ppm.

Additional advantages and features of the present invention will be described more fully in connection with the following drawings, in which:

BRIEF DESCRIPTION OF THE DRAWINGS

FIG. 3b is a range chart which relates to the control chart of FIG. 3a.

FIG. 4b is a range chart which relates to the control chart of FIG. 4a.

DETAILED DESCRIPTION OF THE PREFERRED EMBODIMENT

Figure 1A:
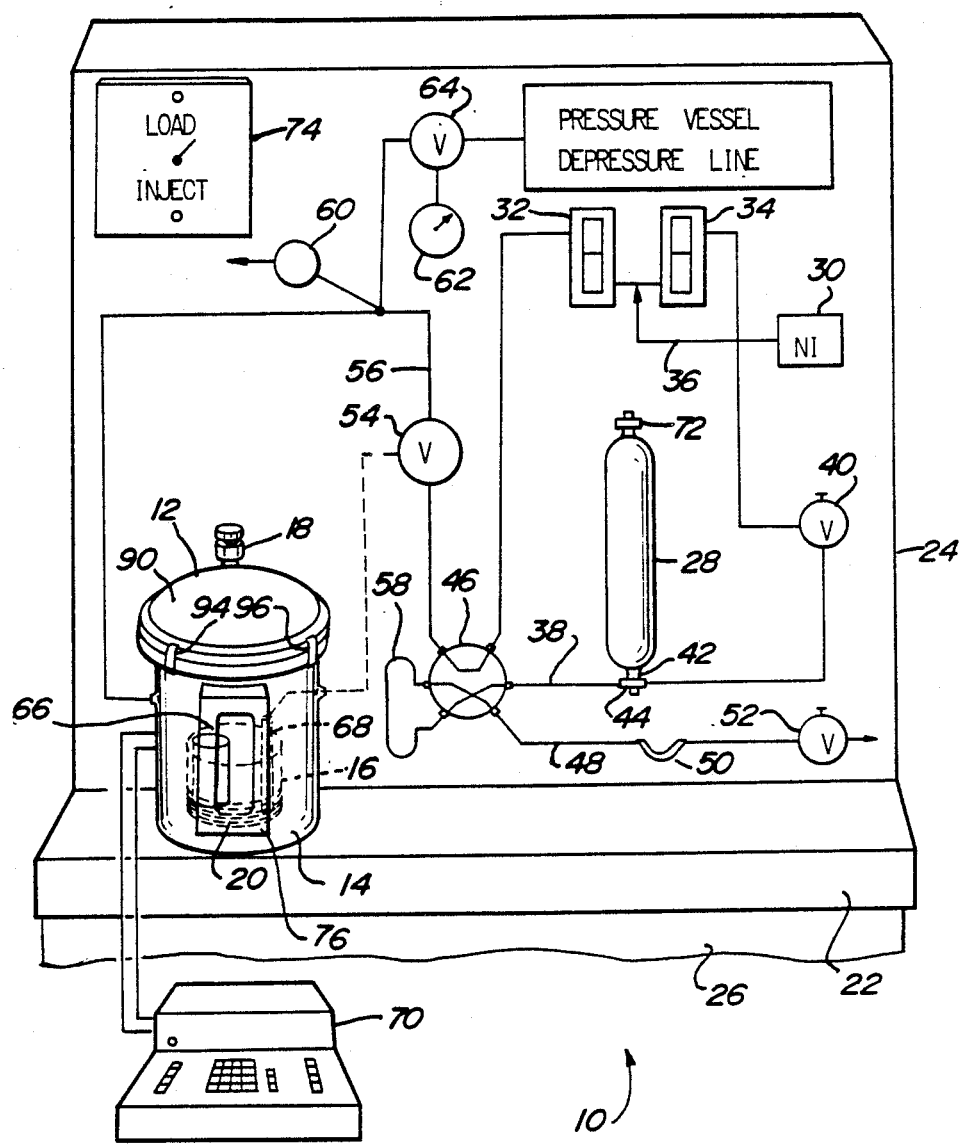
FIG. 1a is a diagramatic representation of the coulometric titration apparatus according to the present invention, which particularly illustrates fluid flow during the "load" made.
Figure 1B:
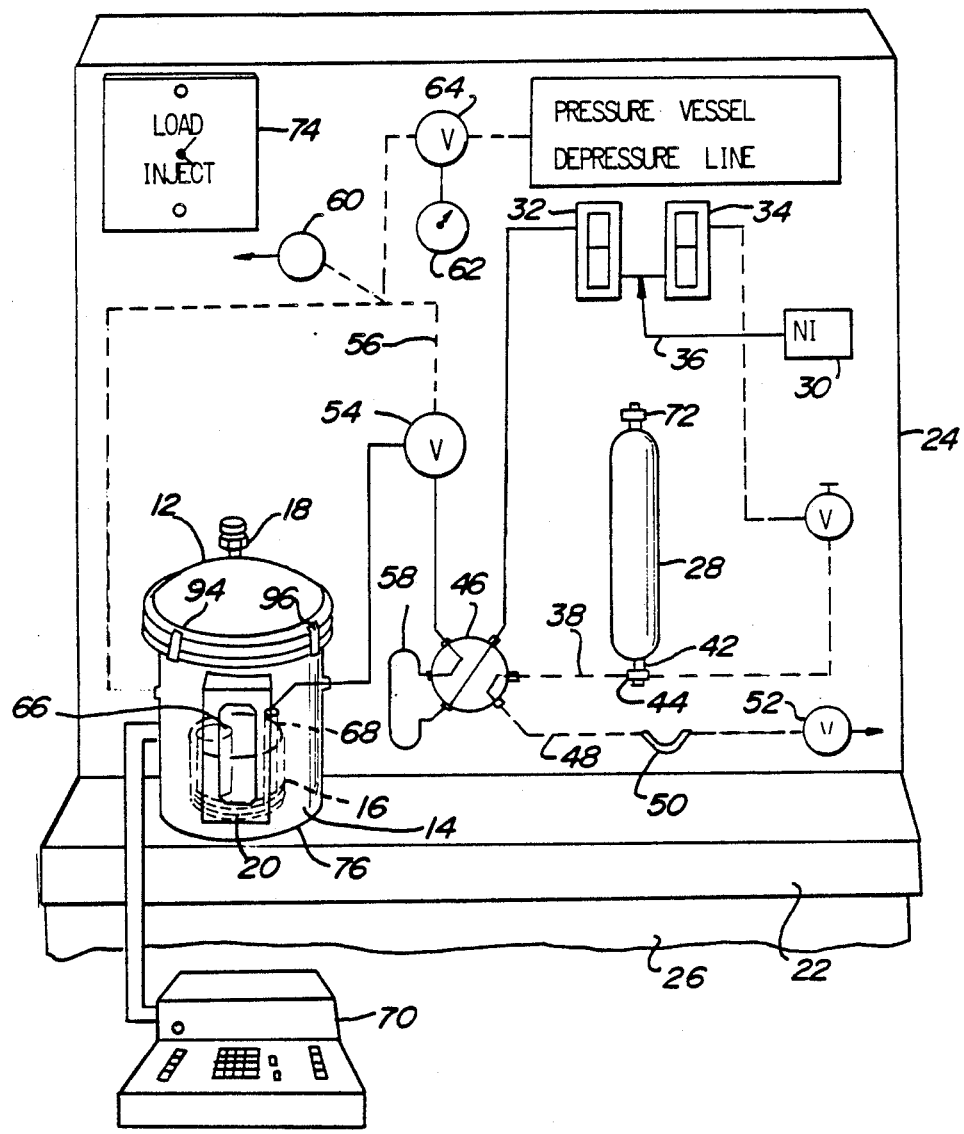
FIG. 1b is a diagramatic representation of the coulometric titration apparatus according to the present invention, which particularly illustrates fluid flow during the "inject" mode.

Referring to FIGS. 1a and 1b, a diagrammatic representation of a coulometric titration apparatus 10 according to the present invention is shown for both the "load" and "inject" modes. The apparatus 10 includes a pressure vessel 12 which is used to create an internal chamber 14 for containing a titration vessel 16. In accordance with the present invention, the pressure vessel 12 is constructed so as to permit the pressure in the chamber 14 to be increased to and maintained at a level which is above the vapor pressure of the sample to be titrated. Such high pressure operation will enable the sample to remain in the liquid phase in order to help insure that all of the water from the sample is trapped in the solvent 20 contained in the titration vessel 16.

Figure 2:
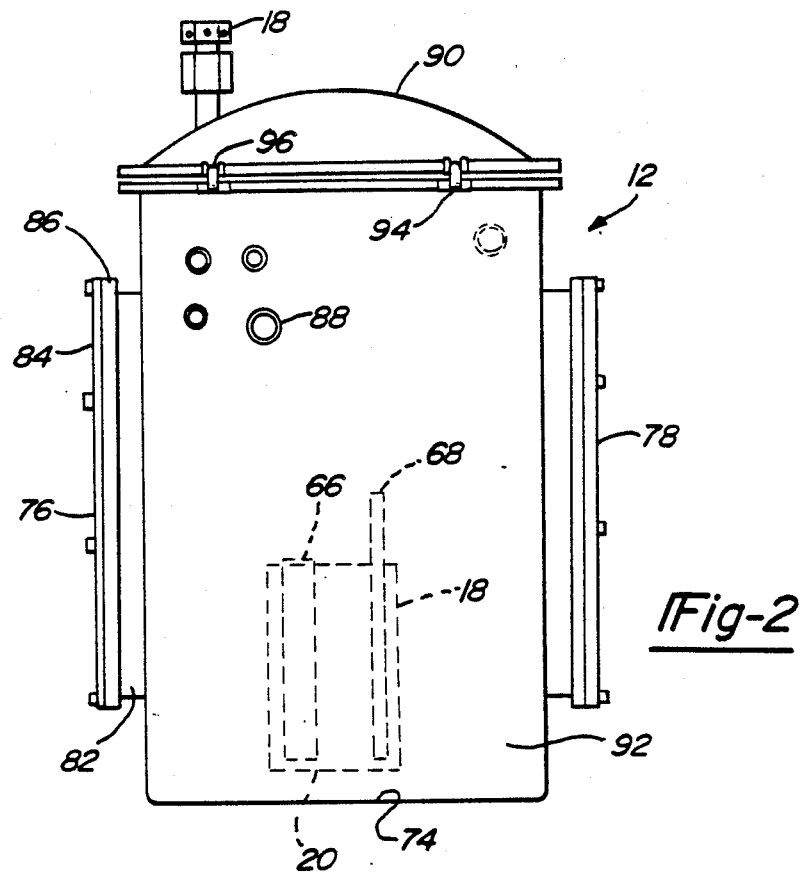
FIG. 2 is an elevation view of the pressure vessel shown in FIG. 1.

While the pressure vessel will be more fully described in connection with FIG. 2, it should be noted that the pressure vessel may be fitted with a rupture disc 18 to protect the integrity of the pressure vessel 12 for future operation, as illustrated in FIG. 1. In this regard, the rupture disc employed should have a pressure rating which will permit operation in the desired range of interest, while yet having a pressure rating which is below the maximum design pressure of the pressure vessel 12. Thus, if the samples being titrated have vapor pressures in the range of 80 to 100 psi, the rupture disc 18 selected should be designed to rupture at a pressure which is comfortably above this pressure range (e.g. at 120 psi).

As shown in FIG. 1a, the apparatus 10 preferably includes a support structure, which generally comprises a platform 22 and a back panel 24. The back panel 24 is mounted to and extends vertically from the rear of the base platform 22. In one form of the present invention, a rectangular base pedestal 26 is also employed to elevate the platform 22. This support structure may be made of any suitable rigid and durable material, such as laminated particle board. The platform 22 is used to support the pressure vessel 12 and a cylinder 28 that contains a supply of the sample to be titrated. The back panel 24 is used to support the various fluid control components for the apparatus 10.

The fluid control components according to the present invention are used to control the flow of the sample liquid from the cylinder 28, as well as control the flow of a dry, inert carrier gas from a source of supply, such as nitrogen cylinder 30. While nitrogen is preferably employed as the carrier gas, other suitable dry gases which are inert to the chemicals to which they will come into contact may be employed in the appropriate application. Gas flow from the nitrogen cylinder 30 is branched into two separate flow meter assemblies 32 and 3 via conduit 36. The conduit 36, as well as most of the other conduits shown in FIG. 1 are preferably made of ⅛ inch stainless steel tubing. However, other suitable conduit materials may be employed which will withstand the operating pressures and not interfere with the chemicals used in the process.

The right hand flow meter assembly 34 includes a valve for regulating the flow rate of nitrogen through a sample supply line 38. The sample supply line 38 includes a manually actuated valve 40 which is used to quickly shut off gas flow from the nitrogen cylinder 30. The sample supply line 38 is coupled to the sample cylinder 28 through another manually actuated valve 42 and a stainless steel tee connector 44. The sample supply line 38 is also connected to a six port sample valve 46 through which gas flow may be directed to a vent line or conduit 48. The vent line 48 leads to a hood for handling waste fluid from the sample supply line 38 and sample valve 46. A vent line 48 includes a length of clear tubing 50 and a shut off valve 52. The clear tubing 50 (e.g., Teflon) is used to determine whether the fluid being conveyed through the vent line 48 at that point is either gas or liquid.

The left hand flow meter assembly 32 also includes a valve for regulating the gas flow rate from the nitrogen cylinder 30. However, in one embodiment according to the present invention, the flow rates through the flow meter assemblies 32 and 34 are set at different levels. Specifically, the flow meter assembly 32 is preferably set at one standard cubic foot/hour, while the flow meter assembly 34 is preferably set at seven standard cubic feet/hour. This is because the flow meter assembly 34 is used to sweep the sample supply line 38 at a relatively high rate in order to insure that it is kept dry. In contrast, the flow meter assembly 32 is set at a relatively low flow rate, as it is used to always keep a small continuous flow of nitrogen to the pressure vessel 12 through the sample valve 46, a three-way valve 54 and a conduit 56. The gas from the flow meter assembly 32 is also used to convey a predetermined volume of the sample to the titration vessel 16 after it has been loaded in a one milliliter sample loop 58 coupled to the sample valve 46.

A back pressure regulator 60 is connected to the conduit 56 in order to control the pressure created within the chamber 14 by the constant flow of gas from the flow meter assembly 32. Specifically, the back pressure regulator 60 operates to vent gas from the system above the set point of the regulator. While the constant flow of gas to the pressure vessel 12 may be unnecessary, it helps to insure that the desired pressure within the chamber 14 will be maintained by the back pressure regulator 60 in the event that there are any leaks in the pressure vessel or connections.

A pressure gauge is also connected to the conduit 56 through another three-way valve 64. In one position, the three-way valve 64 permits fluid communication between the pressure gauge 62 and the conduit 56 in order to monitor the pressure within the chamber 14. In its other position, the three-way valve 64 permits fluid flow from the pressure vessel 12 to a vent through the conduit 56 in order to depressurize the chamber 14 for maintenance purposes.

In one embodiment of the invention, both of the three-way valves 54 and 64 are SS-41S2 valves from Capital Valve, of Baton Rouge. Similarly, the back pressure regulator 60 is a 29-2321-24 from Del Rio Inc., of Baton Rouge. Likewise, the six port valve 46 is a A6UWP 6 Port Valco Valve With Actuator valve from Allometrics, of Baton Rouge. Additionally, the flow meter assemblies 32 and 34 are preferably DK 32 meter valves from D & W Systems, of Baton Rouge.

With respect to the titration vessel 16, FIGS. 1a and 1b show that the titration vessel includes a generating electrode 66 and an indicating probe 68. Both the generating electrode 66 and the indicating probe 68 are electrically connected to a coulometric analyzer 70 which may be conveniently situated near to the pressure vessel 12. The titration vessel should also be equipped with a device for stirring the solvent 20, such as a J-4650-62 stirrer from Cole-Palmer. One of the advantages of the present invention is that the apparatus 10 may utilize existing titration vessel assemblies and coulometric analyzers, such as those shown in FIGS. 1a and 1b. In this regard, these components typically may be purchased as a system such as Metrom Coulometric KF Titrator Model No. 684 from Brinkman Instruments, Inc. of Wesbury, N.Y. However, it should be appreciated that other suitable titration vessel and analyzer systems may be employed, and that this particular titration system has been identified for exemplary purposes only.

With respect to the differences between FIGS. 1a and 1b, FIG. 1a illustrates the apparatus 10 during a "load" model. Whereas, FIG. 1b illustrates the apparatus 10 during an "inject" mode. Prior to the load mode, nitrogen gas will be transmitted through line 38 and the six port valve 46 to the vent in order to ensure that the sample line is dry. Additionally, nitrogen gas from the flow meter assembly 32 will be transmitted through the transport valve 46 and the conduit 56 to maintain the chamber 14 at the desired pressure level. When entering the load mode, the valve 40 will be manually actuated to cut off the flow of nitrogen in the sample line 38, and the valve 42 will be open to convey liquid sample material from the cylinder 28 through the sample line 38, the six port valve 46 to the vent via conduit 48. With the six port valve 46 in the load position, the sample material will flow through the sample loop 58 which is connected to the six port valve. Once it is seen at the clear tubing 50 that liquid is flowing out to the vent, it will be known that the sample loop 58 is filled completely with the liquid sample material. A valve 72 may also be provided at the top of the sample cylinder 28 to provide a connection to a high pressure (e.g., 128 psi) nitrogen gas line to ensure that the sample material within the cylinder 28 remains in a liquid state.

Once the sample loop 58 is completely filled with the liquid sample material from cylinder 28, the six port valve 46 may be switched to the inject position via switch 74. In the inject mode, nitrogen gas from the flow meter assembly 32 will push the liquid sample material in the sample loop 58 through the three way valve 54 and into the indicating probe 68 of the titration vessel 16. After approximately 10 seconds, the six port valve 46 may then be switched back to the load position in order to reset the assembly to a mode where it is ready to collect another sample. Similarly, the three way valve 54 will be manually switched back to a load position, whereby nitrogen gas from the flow meter assembly 32 will again be conveyed to the chamber 14 through conduit 56. As should be appreciated from the above, the apparatus 10 permits a number of samples to be quickly analyzed through this procedure.

Referring to FIGS. 2a and 2b, various elevation views of the pressure vessel 12 are shown. As should appreciated from the figures, the pressure vessel 12 preferably has a cylindrical shape to provide a generally flat bottom wall portion 74 to support the titration vessel 16. In one form of the present invention the pressure vessel is made from 316 stainless steel and is constructed with a pair of opposing window assemblies 76 and 78. The use of two window assemblies permits sufficient light to pass into the chamber 14 so that the titration vessel 16 may be readily inspected visually. Each of the window assemblies 76 and 78 include a rectangular section of glass 80 which is secured to the pressure vessel 12 between a generally rectangular pedestal portion of the pressure vessel and a rectangular bracket 84 which is bolted to a flange 86 of the pedestal portion 82. A Viton o-ring (not shown) may be interposed between the glass section 80 and the bracket 84 and flange 86. While the window assemblies 76 and 78 are preferred, it should be appreciated that a suitable pressure vessel could be constructed without this advantageous feature in the appropriate application.

The pressure vessel 12 also includes a plurality of ports such as port 88 to provide the necessary electrical and fluid connections to the chamber 14. These ports are preferably disposed near to the top of the pressure vessel 12, so that all of the electrical and fluid lines extending into the chamber 14 may be directed downwardly toward the titration vessel 16. The pressure vessel 12 also includes a removable top cover 90 which may have either a domed or flat shape. This cover is preferably mounted to the cylindrical wall 92 of the pressure vessel via a plurality of screws or bolts, such as indicated at reference numerals 94 and 96. The cylindrical wall 92 is formed with a radially extending flange 98 and the cover 90 is formed with a corresponding flange 100. Each of these flanges are preferably provided with a groove to mount a Viton o-ring which helps to provide the necessary seal between the cover 90 and the cylindrical wall 92. After the titration vessel 16 is placed into the chamber 14 of the pressure vessel 12, the cover 90 may be swung closed and bolted to the cylindrical wall 92 at one or more points along the flanges 98 and 100.

Figure 3A:
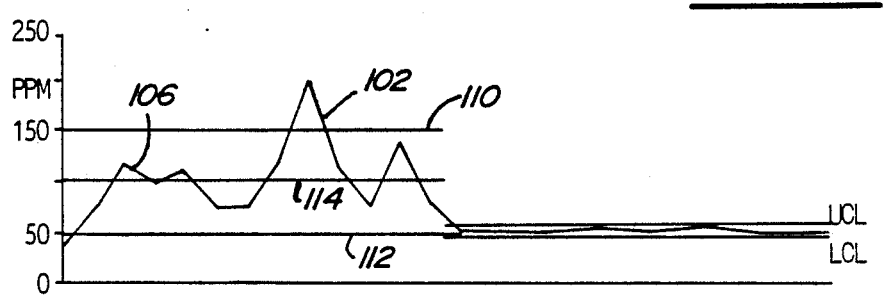
FIG. 3a is a control chart which compares the analysis of water in methyl chloride using conventional Karl Fischer titration, as shown on the left side of the chart, and titration according to the present invention, as shown on the right side of the chart.
Figure 3B:
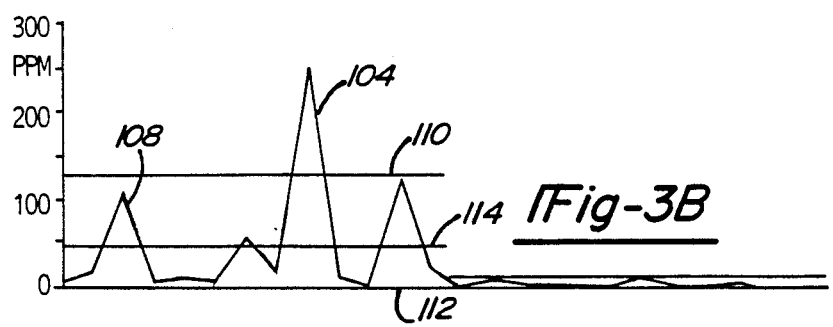

Referring to FIG. 3a, a control chart is shown which compares the analysis of water in methyl chloride using conventional Karl Fischer titration, as shown on the left side of the chart, and titration according to the present invention, as shown on the right side of the chart. Specifically, the left side of the chart illustrates how operator dependent conventional Karl Fischer titration is for analyzing water in methyl chloride. In this regard FIG. 3a shows a curve 102 which was formed by linking a number of points together on the chart. Each of these points represents an average of three samples analyzed by one of three different operators. Each of the samples provided to the operators were taken from the same cylinder, and FIG. 3a shows the wide variation in the average part per million of water found using conventional Karl Fischer titration. FIG. 3b relates to FIG. 3a in that FIG. 3b shows a range chart. In this regard, the range chart includes a curve 104 which was formed by linking each of the separate points in the chart together.

Each of the points in the range chart indicate the range for each of the corresponding points in the control chart of FIG. 3a. In other words, for the point 106 in t he control chart, the corresponding point 108 in the range chart of FIG. 3b indicates that the spread between the highest and lowest of the three samples analyzed was 110 ppm of water. Each of the charts in FIGS. 3a and 3b include an upper control limit line 110, a lower control limit line 112 and a line 114 which represents the average of all the points in the graph.

Turning to the right-hand side of both FIG. 3a and FIG. 3b this portion of these two charts represents a similar experiment conducted with a different sample from that employed for the left-hand side of the charts using the method according to the present invention. Accordingly, it should be appreciated from these two charts that the variability in the results achieved by the different operators was very low in comparison to the variability seen using conventional Karl Fischer titration.

Figure 4A:
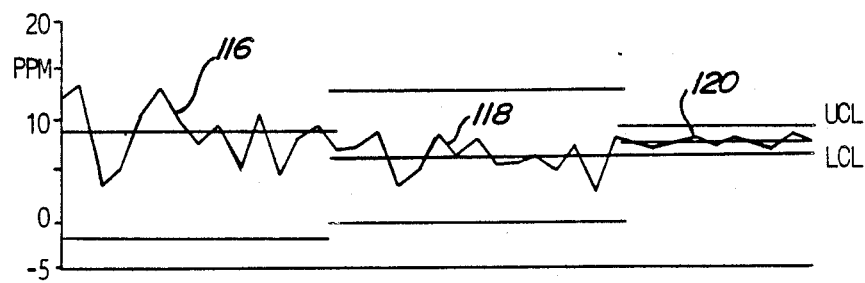
FIG. 4a is a control chart which compares the analysis of water in vinyl chloride using conventional Karl Fischer titration, as shown on the left side and center portion of the chart, and titration according to the present invention, as shown on the right side of the chart.
Figure 4B:
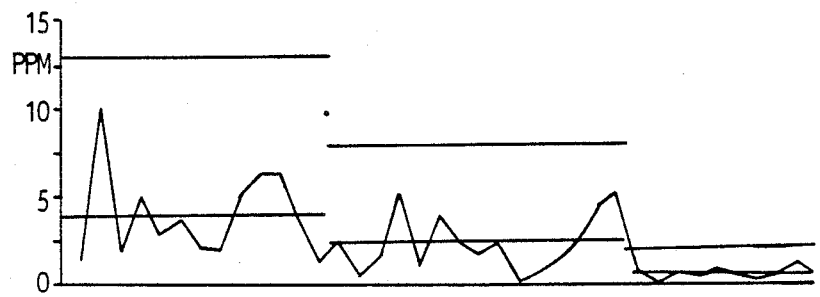

Turning to FIG. 4a, a control chart is shown which compares the analysis of water in vinyl chloride using Karl Fischer titration as shown on the left side and center portion of the chart, and titration according to the present invention, as shown on the right side of the chart. The left-hand and center portions of the control chart of FIG. 4a represent the analysis of the same sample material achieved repeatedly using different operators. In other words, the left-hand portion of the chart shows a curve 116 constructed from the analysis by one operator, whereas the center portion of the chart includes a curve 118 constructed from the analysis by a different operator. Finally, the right-hand side of the chart shows a curve 120 which represents that analysis achieved by one of the previous two operators utilizing the method according to the present invention. While the average lines for each of these three graph portions are different, it should be readily appreciated that the variability of curve 120 is considerably less than the variability of either curves 116 and 118. Similarly, independence of the present invention from the technique of a particular operator is also confirmed in the range chart of FIG. 4b for the control chart of FIG. 4a.

FIG. 4A also illustrates that it is possible to detect water in liquid samples below the 10 ppm level using the present invention. This represents one of the significant advantages of the present invention, and in this regard, it may be found useful to increase the volume of the sample loop (e.g., 5 milliliters) when working in this range.

While it will be apparent that the teachings herein are well calculated to teach one skilled in the art the apparatus and method according to the present invention, it will be appreciated that the invention is susceptible to modification, variation and change without departing from the proper scope and meaning of the sub-joined claims.

What is claimed is:

1. A coulometric titration apparatus for enabling a sample which is normally a vapor under atmospheric conditions to be analyzed in the liquid phase, comprising:

pressure vessel means for providing a chamber capable of being subjected to a predetermined pressure level which is above the vaporization level of said sample, said pressure vessel means being constructed to contain a titration vessel and permit said titration vessel to communicate with a coulometric titration analyzer;

regulator means for causing the pressure in said chamber to be maintained at said predetermined level; and fluid control means for enabling said chamber to be purged with an inert gas and for injecting said sample into said titration vessel from a source of said sample.

2. The invention according to claim 1, wherein said pressure vessel means includes a movable wall portion for permitting access to said chamber, and port means for enabling electrical and fluid communication with said chamber.

3. The invention according to claim 2, wherein said pressure vessel means includes window means for permitting visual inspection of said chamber.

4. The invention according to claim 2, wherein said pressure vessel means is constructed of stainless steel, and said pressure vessel means includes a rupture disc having a rupture point above said predetermined pressure level.

5. The invention according to claim 2, wherein said movable wall portion is a top cover, and said port means is comprised of a plurality of ports which are all located near to said top cover of said pressure vessel means.

6. The invention according to claim 1, wherein said regulator means includes a back pressure regulator which is in fluid communication with said chamber.

7. The invention according to claim 6, wherein said regulator means includes valve means for depressurizing said chamber.

8. The invention according to claim 1, wherein said fluid control means includes a multi-port valve having a sample loop for defining a predetermined volume of said sample to be conveyed to said titration vessel, and an injection valve for controlling fluid communication between said sample source and said multi-port valve.

9. The invention according to claim 8, wherein said fluid control means includes conduit means for providing fluid communication between a source of said inert gas and said injection valve with an input port of said multi-port valve.

10. The invention according to claim 9, wherein said fluid control means further includes a three-way valve having its input port in fluid communication with an output port of said multi-port valve.

11. The invention according to claim 10, wherein one outlet port of said three-way valve is in fluid communication with said chamber for conveying said inert gas from said multi-port valve to said chamber, and another outlet port of said three-way valve is in communication with said titration vessel for conveying said sample from said multi-port valve to said titration vessel.

12. The invention according to claim 9, wherein said multi-port valve has one position for loading said sample loop from said sample source and another position for injecting said sample contained in said sample loop into said titration vessel using fluid flow from said inert gas.

13. A method of analyzing a sample by coulometric titration which is normally a vapor under atmospheric conditions, comprising the steps of:

enclosing a titration vessel within a chamber capable of being pressurized;

subjecting said chamber to a predetermined pressure level which is above the vaporization pressure of said sample by injecting an inert gas into said chamber;

loading a sample into a container which provides a predetermined volume; and injecting said sample from said container into said titration vessel for analysis.

14. The method according to claim 13, wherein said container is a sample loop connected to a multi-port valve.

15. The method according to claim 14, wherein said sample is injected into said titration vessel from said sample loop by switching the position of said multi-port valve, so that fluid flow from a source of said inert gas causes said sample to be conveyed into said titration vessel.

* * * * *